United States Patent [19]

Poletto et al.

[11] Patent Number: 4,968,702

[45] Date of Patent: Nov. 6, 1990

[54] SUBSTITUTED QUINOLINECARBOXYLIC ACIDS

[75] Inventors: John F. Poletto, Westwood, N.J.; Dennis W. Powell, Valley Cottage, N.Y.; Diane H. Boschelli, Novi, Mich.

[73] Assignee: American Cyanamid Company, Stamford, Conn.

[21] Appl. No.: 298,585

[22] Filed: Jan. 17, 1989

[51] Int. Cl.$^5$ ..................... A61K 31/47; C07D 215/38
[52] U.S. Cl. .................................... 514/313; 546/159; 546/160; 546/162
[58] Field of Search ............... 546/159, 160, 162, 168, 546/169, 170, 163; 514/313, 311

[56] References Cited

U.S. PATENT DOCUMENTS 2,888,346  5/1959  Tulagin et al. .................. 96/84
4,680,299  7/1987  Hesson ............................ 514/311

FOREIGN PATENT DOCUMENTS 287804  10/1915  Fed. Rep. of Germany .
288865  11/1915  Fed. Rep. of Germany .

OTHER PUBLICATIONS

Berlingozzi et al., Chem. Abs. vol. 21, pp. 2473–2474 (1927).
Berlingozzi et al., Ann. Chim. applicata, 17, pp. 250–256 (1927).
Berlingozzi et al., A. A. Lincei. Rend. Classe Sci., 32, 403–406 (1923).
John, J. Prakt. Chem., 133, 259–272 (1932).
De Diesbach et al., Helv. Chim. Acta, 20, 132–141 (1937).
Petrow et al., J. Chem. Soc., 316–318 (1943).
Colonna et al., Gazz. Chim. Ital., 78, 787–793 (1948).
Cragoe et al., J. Org. Chem., 18, 561–569 (1953).
Atkinson et al., J. Chem. Soc., 3718–3721 (1957).
Ardashev et al., Khim. Geterotsikl. Soedin., 4, 525–526 (1972).

Primary Examiner—Mukund J. Shah
Assistant Examiner—Edward C. Ward
Attorney, Agent, or Firm—Alan M. Gordon

[57] ABSTRACT

Substituted quinolinecarboxylic acids useful in the treatment of arthritis by inhibiting the progressive joint deterioration characteristic of arthritic disease and for inducing immunosuppression are disclosed. Methods of synthesis and use of the novel compounds are also disclosed.

45 Claims, No Drawings

SUBSTITUTED QUINOLINECARBOXYLIC ACIDS

SUMMARY OF THE INVENTION

This invention is concerned with new compounds of the formula I:

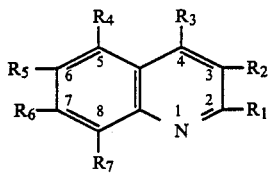

Formula I wherein $R^1$ is selected from the group consisting of

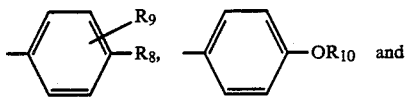

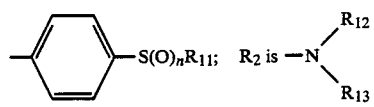

$R_3$ is selected from the group consisting of

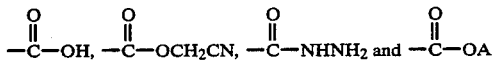

where A is an alkali or alkaline earth metal); $R_4$, $R_5$, $R_6$ and $R_7$ are independently selected from the group consisting of hydrogen, halogen, alkyl($C_1$-$C_6$), trifluoromethyl and -O-alkyl($C_1$-$C_4$), with the proviso that least two of $R_4$, $R_5$, $R_6$ and $R_7$ must be hydrogen; $R_8$ is selected from the group consisting of straight or branched chain alkyl($C_1$-$C_{12}$, halogen, cycloalkyl($C_3$-$C_7$), trifluoromethyl, hydroxy, phenyl, 2-fluorophenyl and pyridyl; $R_{10}$ is selected from the group consisting of

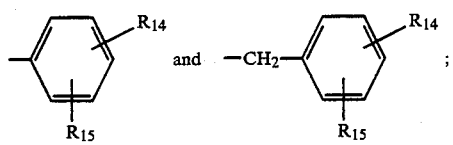

$R_{12}$ is selected from the group consisting of hydrogen and alkyl($C_1$-$c_6$); $R_{13}$ is selected from the group consisting of hydrogen, alkyl($C_1$-$C_6$),

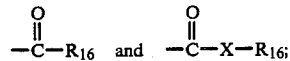

$R_{16}$ is alkyl ($C_1$-$C_6$),

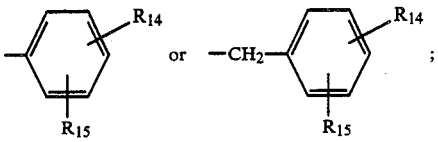

X is —O—, —S—, —NH— or $NR_{16}$; $R_{11}$ is selected from the group consisting of straight or branched chain alkyl($C_1$-$C_{12}$), cycloalkyl ($C_1$-$C_7$), trifluoromethyl, hydroxy, phenyl and 2-fluorophenyl; $R_9$, $R_{14}$ and $R_{15}$ are independently selected from the group consisting of hydrogen, halogen, nitro, alkyl ($C_1$-$C_5$), alkoxy ($C_1$-$C_5$), alkylthio ($C_1$-$C_5$), hydroxy, trifluoromethyl and amino; n is an integer from zero to two inclusive; and the pharmacologically acceptable salts thereof.

This invention is also concerned with methods of treating arthritis in a mammal by inhibiting the progressive joint deterioration characteristic of arthritic disease and with methods of inducing immunosuppression in a mammal which comprises administering to said mammal an effective amount of a compound selected from those of formula I, together with pharmaceutical compositions of matter containing compounds selected from those of formula I and methods for the preparation of the compounds of formula I.

Further, this invention is concerned with compounds of the formula II:

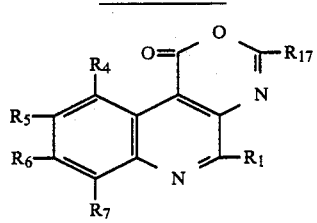

Formula II wherein $R_1$, $R_4$, $R_5$, $R_6$ and $R_7$ are defined as in formula I and $R_{17}$ is selected from the group consisting of hydrogen and alkyl ($C_1$-$C_6$). The compounds of formula II find utility as intermediates used in the preparation of the compounds of formula I.

DESCRIPTION OF THE INVENTION

The compounds of this invention may be prepared according to one or more of the following reaction schemes:

Scheme A

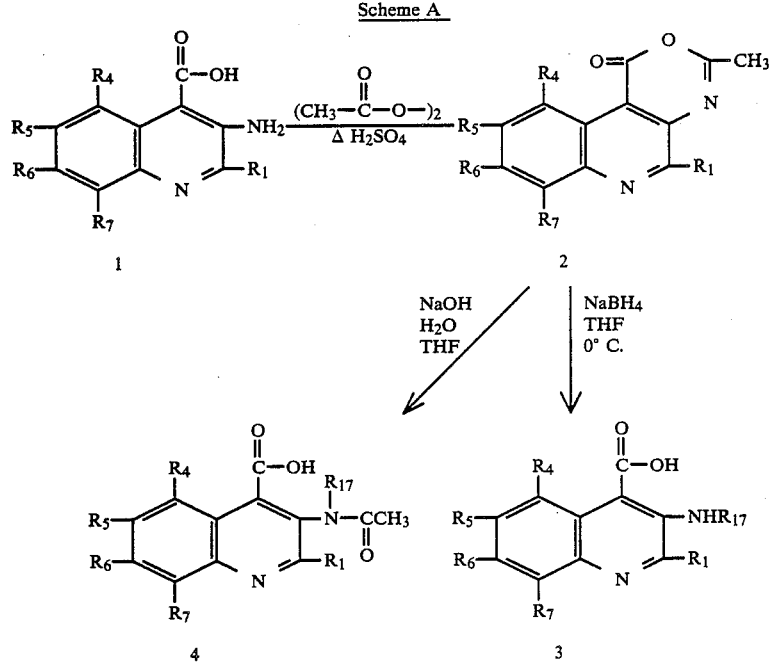

According to Scheme A, a substituted quinolinecarboxylic acid 1, where $R_1$, $R_4$, $R_5$, $R_6$ and $R_7$ are as described above, is reacted with acetic anhydride and a catalytic amount of concentrated sulfuric acid at 90° C., giving a substituted 3-methyl-1H-[1,3]oxazino[4,5-c]quinoline-1-one 2 which is then reacted with sodium borohydride in tetrahydrofuran at 0° C., giving the substituted-4-quinolinecarboxylic acid 3, where $R_{17}$ is alkyl ($C_1$–$C_{16}$). The derivative 2 may also be basified in water and tetrahydrofuran and then acidified, giving the 3-acetylamino derivative 4.

Scheme B

According to Scheme B, a substituted isatin 5, where $R_4$, $R_5$, $R_6$ and $R_7$ are as described above, is suspended in water, basified, heated to 80°–95° C. and reacted at reflux with an ethanolic/aqueous solution of a 2-amino-4'-substituted acetophenone hydrochloride salt 6, where $R_1$ is as described above, then evaporated and acidified, giving 2-amino-substituted quinolinecarboxylic acids 7.

The compounds of the present invention are active immunosuppressive agents when administered to warm-blooded animals. As such they are effective in treating conditions where elevated levels of antibody production or monocyte/lymphocyte activity as a result of the hyperreactivity of immunoregulatory network are closely associated with the development of autoimmune diseases, including rheumatoid arthritis [Mellbye, O. J. and Natvig, J. B., Clin. Exp. Immunol., 8, 889 (1971)]; multiple sclerosis [Tourtellotte, W. W. and Parker, J. A., Science 154, 1004 (1966)]; systemic lupus erythematosis [Abdu, N. I., et al., Clin. Immunol. Immunopath., 6, 192 (1976)]; thyroiditis [Witebsky, E., et al., J. Immunol., 103, 708 (1969)]; mixed connective tissue disease [Sharp, G. C., et al., Am. J. Med., 52, 148 (1972)]; dermato/polymyositis [Venables, P. J. W., et al., Ann. Rheum. Dis., 40, 217 (1981)]; insulin-dependent diabetes [Charles, M. A., et al., J. Immunol., 130, 1189 (1983)] and in patients undergoing organ transplantation.

The immunosuppressive activity of representative compounds of this invention was established in the following test.

Chronic Graft versus Host (GvH) Reaction

The reaction is induced by injection of $100 \times 10^6$ DBA/2 spleen cells from male mice, 6–8 weeks of age, into age-matched DBA/2×C57B1−6F$_1$)(BDF$_1$) male mice. Seven days post injection oral dosing with a test drug is begun and continued for 14 consecutive days. At this time (21 days after injection of cells), the BDF$_1$ mice are bled and their serum analyzed for autoantibody to DNA by enzyme linked immunosorbent assay (ELISA).

The ELISA is performed as follows:
(1) Polystyrene microtiter plates are coated overnight at 4° C. with 10 μg/ml of heat denatured DNA from mouse Ehrlich Ascites cells.
(2) The wells are washed twice with phosphate buffered saline (PBS) and incubated for 2 hours with 10% horse serum in PBS at room temperature.
(3) The wells are washed twice with PBS containing 0.1% Tween 20 and are then incubated with serum samples diluted at 1/200, 1/400 and 1/800. Serum from the autoimmune strain of mice MRL lpr/lpr is used as a positive control and serum from normal $F_1$ mice as negative control.
(4) After overnight incubation at 4° C., the microtiter plates are washed three times with PBS (0.1% Tween 20)-1% bovine serum albimin (BSA) and a 1/2000 dilution of goat anti mouse IgG coupled to alkaline phosphatase is added to the wells. The enzyme-antibody conjugate is incubated for 3 hours at room temperature.
(5) The plates are washed three times with buffer as above and 200 μl of a 0.25 mg/ml solution of p-nitrophenyl phosphate in 1.0M Tris-HCl buffer pH 8.0. After 45 minutes, the reaction is stopped with 60 μl of 13% $K_2HPO_4$ and the amount of anti DNA antibody is quantitated by reading the plates on a spectrophotometer at 405 nm.

A test compound is considered active if it causes a 40–50% decrease in the absorbance at 405nm (A 405) of the vehicle treated GvH mice.

The results of this test on representative compounds of the present invention appear in Table I.

TABLE I

| Chronic GvH Reaction | | | | |
|---|---|---|---|---|
| | Dose (mg/kg) | GvH | Anti DNA Autoantibody A405 | Percent Suppression |
| None | | − | * | |
| Vehicle | | + | .206 | |
| 3-Amino-6-fluoro-2-(4-phenoxyphenyl)-4-quinoline-carboxylic acid | 50 | + | .114 | 45 |
| None | | − | .015 | |
| Vehicle | | + | .615 | |
| 2-[1,1'-Biphenyl]-4-yl-6-fluoro-3-(methylamino)-4-quinolinecarboxylic acid | 50 | + | .080 | 87 |
| 3-(Acetylamino)-2-[1,1'-biphenyl]-4-yl-6-fluoro-4-quinolinecarboxylic acid | 50 | + | .433 | 30 |
| 3-(Acetylethylamino)-2-[1,1'-bipheny]-4-yl-6-fluoro-4-quinolinecarboxylic acid | 50 | + | .751 | |
| None | | − | * | |
| Vehicle | | + | .206 | |
| 3-Amino-2-[1,1'-biphenyl]-4-yl-6-iodo-4-quinoline-carboxylic acid | 50 | + | .005 | 98 |
| 3-Amino-2-[1,1'-biphenyl]-4-yl-6-chloro-4-quinoline-carboxylic acid | 50 | + | .139 | 33 |
| None | | − | * | |
| Vehicle | | + | .446 | |
| 3-Amino-2-(4-phenoxyphenyl)-4-quinoline-carboxylic acid | 50 | + | .269 | 40 |
| None | | − | * | |
| Vehicle | | + | .310 | |
| 3-Amino-2-[1,1'-biphenyl]-4-yl-6-fluoro-4-quinolineacarboxylic acid | 25 | + | .011 | 96 |
| None | | − | .018 | |
| Vehicle | | + | .285 | |
| 2-[1,1'-Biphenyl]-4-yl-3-(ethylamino)-6-fluoro-4-quinolinecarboxylic acid | 50 | + | .224 | 21 |
| None | | − | * | |
| Vehicle | | + | .315 | |
| 3-Amino-6-chloro-2-(2'-fluoro[1,1'-biphenyl)]-4-yl)-4-quinolinecarboxylic acid | 50 | + | .026 | 92 |
| None | | − | * | |
| Vehicle | | + | .323 | |
| 3-Amino-2-[1,1'-biphenyl]-4-yl-trifluoromethyl-4-quinolinecarboxylic acid | 50 | + | .003 | 99 |
| None | | − | * | |
| Vehicle | | + | 315 | |
| 2-[1,1'-Biphenyl]-4-yl-3-(dimethylamino)-6-fluoro-4-quinolinecarboxylic acid | 50 | + | .063 | 80 |
| 3-Amino-6-fluoro-2-[4-(trifluoromethyl)-phenyl]-4-quinolinecarboxylic acid | 50 | + | .023 | 93 |
| Vehicle | | + | .308 | |
| 3-Amino-6-fluoro-2-(4-chlorophenyl)-4-quinolinecarboxylic acid | 50 | + | .294 | 5 |
| None | | − | * | |
| Vehicle | | + | .323 | |
| 3-Amino-6-chloro-2-(4'-fluoro[1,1'-biphenyl]-4-yl)-4-quinolinecarboxylic acid | 50 | + | .013 | 96 |
| None | | − | * | |
| Vehicle | | + | .308 | |
| 3-Amino-6-fluoro-2-(4-bromophenyl)-4-quinolinecarboxylic acid | 50 | + | .246 | 20 |
| | 50 | + | .246 | 20 |
| 3-Amino-6-iodo-2-(2'-fluoro[1,1-biphenyl]-4-yl)- | 50 | + | .138 | 55 |

TABLE I-continued

| | Chronic GvH Reaction | | | |
|---|---|---|---|---|
| | Dose (mg/kg) | GvH | Anti DNA Autoantibody A405 | Percent Suppression |
| 4-quinolinecarboxylic acid 3-Amino-6-chloro-2-(bromophenyl)-4-quinolinecarboxylic acid | 50 | + | .416 | |
| 3-Amino-6-chloro-2-(4-chlorophenyl-4-quinolinecarboxylic acid | 50 | + | .220 | 29 |
| 3-Amino-2-(2'-fluoro[1,1'-biphenyl]-4-quinolinecarboxylic acid | 50 | + | .113 | 63 |

* = Not measured

In addition, these compounds are effective in treating inflammation and joint deterioration associated with arthritic disease in warm-blooded animals as established in the following test.

Induction of Adjuvant Arthritis

Outbred, male, Charles River Wistar rats (Willmington, Mass.) weighing approximately 165 g, were injected intradermally in the right hind paw with killed and dried Mycobacterium tuberculosis emulsified in mineral oil (adjuvant) at a dose of 2 mg/kg of body weight. This protocol for induction of arthritis has been described in detail by A. E. Sloboda and A. C. Osterberg, Inflammation, 4, 15 (1976).

Seven days subsequent to immunization with Freund's complete adjuvant, the rats were divided into groups and treated daily by gavage with various doses of the test compounds. Control groups of rats were immunized with adjuvant, but then treated only with starch vehicle.

At the end of 23 days post adjuvant immunization, the left hind paw diameters of all the rats were measured around the ankle joint with a vernier caliper.

The results of this test on representative compounds of this invention are shown in Table II. A paw diameter less than that obtained for control groups indicated a reduction in the induction of arthritis. An enhanced weight gain indicated a lack of toxicity of the test compounds in the treated animals.

The statistical significance of differences between control and treated group were calculated using Student's t test.

TABLE II

Adjuvant Induced Arthritis

| Compound | Daily Dose (mg/kg) | No. of Animals | Mean Final Rat wt. (gm) | Mean Arthritic Paw Diameter (mm) |
|---|---|---|---|---|
| Arthritic Controls (Pooled) | — | 216 | 222 | 11.5 |
| 3-Amino-2-[1,1'-biphenyl]-4-yl-6-fluoro-4-quinolinecarboxylic acid | 6.25 | 72 | 250* | 9.6* |
| 3-Amino-2-[1,1'-biphenyl]-4-yl-6-bromo-4-quinolinecarboxylic acid | 6.25 | 9 | 289* | 9.1* |
| 3-Amino-2-[1,1'-biphenyl]-4-yl-4-quinolinecarboxylic acid | 25.0 | 9 | 229 | 10.5 |
| 2-[1,1'-Biphenyl]-4-yl-3-(ethylamino)-6-fluoro-4-quinolinecarboxylic acid | 25.0 | 9 | 295* | 8.7* |
| 3-Amino-6-fluoro-2-(4-phenoxyphenyl)-4-quinolinecarboxylic acid | 25.0 | 54 | 266* | 8.5* |
| 2-[1,1'-Biphenyl]-4-yl-6-fluoro-3-(methylamino)-4-quinolinecarboxylic acid | 25.0 | 9 | 244* | 8.7* |
| 3-(Acetylethylamino)-2-[1,1'-biphenyl]-4-yl-6-fluoro-4-quinolinecarboxylic acid | 25.0 | 9 | 221 | 10.8 |
| 3-Amino-2-[1,1'-biphenyl]-4-yl-6-chloro-4-quinolinecarboxylic acid | 6.25 | 54 | 248* | 9.3* |
| 3-Amino-2-[1,1'-biphenyl]-4-yl-6-iodo-4-quinolinecarboxylic acid | 25.0 | 18 | 244* | 9.3* |
| 3-Amino-2-(4-phenoxyphenyl)-4-quinolinecarboxylic acid | 25.0 | 9 | 202 | 11.6 |
| | 50.0 | 9 | 234 | 10.4 |
| 3-Amino-2-[1,1'-biphenyl]-4-yl-6,8-dichloro-4-quinolinecarboxylic acid | 12.5 | 18 | 246 | 9.0* |
| 3-Amino-2-[1,1'-biphenyl]-4-yl-6-ethyl-4-quinolinecarboxylic acid | 25.0 | 9 | 293* | 9.5* |
| 3-Amino-6-fluoro-2-(2'-fluoro[1,1'-biphenyl]-4-yl)-4-quinolinecarboxylic acid | 6.25 | 9 | 241 | 8.0* |
| | 3.13 | 18 | 260* | 7.6* |
| 3-Amino-6-fluoro-2-[4-(phenylthio)phenyl]-4-quinolinecarboxylic acid | 12.5 | 9 | 251* | 7.8* |
| 3-Amino-2-[1,1,'-biphenyl]-4-yl-6-trifluoromethyl-4-quinolinecarboxylic acid | 25.0 | 9 | 259* | 9.2* |
| 3-Amino-2-[1,1'-biphenyl]-4-yl-6-fluoro-4-quinolinecarboxylic acid, monosodium salt | 12.5 | 18 | 248* | 8.1* |
| 3-(Acetylamino)-2-[1,1'-biphenyl]-4-yl-6-fluoro-4-quinolinecarboxylic acid | 25.0 | 9 | 207 | 12.1 |
| 3-Amino-6-chloro-2-(2'-fluoro[1,1'-biphenyl]-4-yl-4-quinolinecarboxylic acid | 3.13 | 18 | 251* | 7.7* |
| 2-[1,1'-Biphenyl]-4-yl-3-(dimethylamino)-6-fluoro-4-quinolinecarboxylic acid | 25.0 | 9 | 213 | 11.3 |
| 3-Amino-6-fluoro-2-[4-(trifluoromethyl) | 25.0 | 18 | 253* | 7.6* |

TABLE II-continued

Adjuvant Induced Arthritis

| Compound | Daily Dose (mg/kg) | No. of Animals | Mean Final Rat wt. (gm) | Mean Arthritic Paw Diameter (mm) |
|---|---|---|---|---|
| phenyl]-4-quinolinecarboxylic acid | | | | |
| 3-Amino-6-trifluoromethyl-2-2'-fluoro [1,1'-biphenyl]-4-yl)-4-quinolinecarboxylic acid | 3.13 | 18 | 244* | 8.0* |
| 3-Amino-6-fluoro-2-(4-chlorophenyl)-4-quinolinecarboxylic acid | 25.0 | 9 | 219 | 9.3* |
| 3-Amino-2-(4-chlorophenyl)-4-quinolinecarboxylic acid | 25.0 | 9 | 229 | 10.8 |
| 3-Amino-6,8-dichloro-2-(4-chlorophenyl)-4-quinolinecarboxylic acid | 25.0 | 9 | 235 | 11.8 |
| 3-Amino-6-fluoro-2-(4-bromophenyl-4-quinolinecarboxylic acid | 25.0 | 9 | 224 | 10.8 |
| 3-Amino-6-chloro-2-(4'-fluoro[1,1'-biphenyl]-4-yl)-4-quinolinecarboxylic acid | 6.25 | 18 | 252* | 8.9* |
| 3-Amino-6-trifluoromethyl-2-4-phenoxyphenyl-4-quinolinecarboxylic acid | 25.0 | 9 | 226 | 9.9* |
| 3-Amino-6-trifluoromethyl-2-[4-trifluoromethyl)phenyl]-4-quinolinecarboxylic acid | 25.0 | 18 | 263* | 8.4* |
| 3-Amino-2-(2'-fluoro[1,1'-biphenyl]-4-yl)-4-quinolinecarboxylic acid | 12.5 | 9 | 256* | 8.9* |
| 3-Amino-6-iodo-2-(2'-fluoro[1,1'-biphenyl]-4-yl)-4-quinolinecarboxylic acid | 12.5 | 9 | 261* | 8.8* |
| 3-Amino-6-chloro-2-(bromophenyl)-4-quinolinecarboxylic acid | 25.0 | 9 | 232 | 9.4* |
| 3-Amino-6-chloro-2-(4-iodophenyl)-4-quinolinecarboxylic acid | 25.0 | 18 | 262* | 9.0* |
| 3-Amino-6-fluoro-2-(4-iodophenyl)-4-quinolinecarboxylic acid | 25.0 | 9 | 227 | 10.2* |
| 3-Amino-6-fluoro-2-(2',4'-difluoro[1,1'-biphenyl]-4-yl-quinolinecarboxylic acid | 3.13 | 18 | 244* | 8.5* |
| 3-Amino-6-chloro-2-(2',4'-difluoro[1,1'-biphenyl]-4-yl)-4-quinolinecarboxylic acid | 6.25 | 18 | 259* | 8.0* |
| 3-Amino-2-(2',4'-difluoro[1,1'-biphenyl]-4-yl)-4-quinolineacarboxylic acid | 12.5 | 18 | 247* | 9.3* |
| 3-Amino-6-chloro-2-(4'-fluoro[1,1'-biphenyl]-4-yl)-4-quinolinecarboxylic acid | 12.5 | 9 | 256* | 8.9* |

*Statistically significant suppression of arthritic paw diameter of enhancement of weight gain relative to the arthritic controls.
$p = < .05$ by Student's t test.

The inhibition of progressive joint deterioration was demonstrated by the following test.

Inhibition of Progressive Joint Destruction

This protocol is identical to the experiment whose results were described in Table II. At the end of 23 days the rats were killed, their left hind paws amputated and radiographic evaluation was made as follows: Joint roentgraphs of the left hind paws were prepared on Polaroid x-ray film (type 55) using a Faxitron x-ray unit (Model 43805-N, Hewlett Packard, McMinville, Oreg.). The focus to film distance was 45 cm and the exposure to the x-ray source was 5 minutes at 60KVP. Each radiograph was graded (blind) for the presence and severity of the following parameters:
(a) juxtaarticular erosions of the tarsal bones; and
(b) cartilage space narrowing.

A grade of 0 to 4 (with 0=normal and 4=severe changes) was assigned to each of the parameters.

Again the statistical significance between arthritic controls and treated rats were determined by the use of Students t test. The results of this test on representative compounds of this invention are shown in Table III.

TABLE III

Inhibition of Induced Joint Deterioration

| Compound | Daily Dose (mg/kg) | No. of Animals | Mean X-Ray Score Erosions | Cartilage Space |
|---|---|---|---|---|
| Arthritic Controls (historical) | — | 216 | 3.3 | 3.1 |
| 3-Amino-2-[1,1'-biphenyl]-4-yl-6-fluoro-4-quinolinecarboxylic acid | 6.25 | 72 | 0.9* | 1.4* |
| 3-Amino-2-[1,1'-biphenyl]-4-yl-6-bromo-4-quinolinecarboxylic acid | 6.25 | 9 | 1.4* | 1.4* |
| 3-Amino-2-[1,1'-biphenyl]-4-yl-4-quinolinecarboxylic acid | 25.0 | 9 | 1.2* | 1.6* |
| 2-[1,1'-Biphenyl]-4-yl-3-(ethylamino)-6-fluoro-4-quinolinecarboxylic acid | 25.0 | 9 | 1.0* | 0.8* |
| 3-Amino-6-fluoro-2-(4-phenoxyphenyl)-4-quinolinecarboxylic acid | 25.0 | 54 | 0.9* | 1.0* |
| 2-[1,1'-Biphenyl]-4-yl-6-fluoro-3-(methylamino)-4-quinolinecarboxylic acid | 25.0 | 9 | 1.0* | 0.4* |
| 3-(Acetylethylamino)-2-[1,1'-biphenyl]- | 25.0 | 9 | 1.7* | 2.6 |

TABLE III-continued
Inhibition of Induced Joint Deterioration

| Compound | Daily Dose (mg/kg) | No. of Animals | Mean X-Ray Score Erosions | Mean X-Ray Score Cartilage Space |
|---|---|---|---|---|
| 4-yl-6-fluoro-4-quinolinecarboxylic acid | | | | |
| 3-Amino-2-[1,1'-biphenyl]-4-yl-6-chloro-4-quinolinecarboxylic acid | 6.25 | 54 | 1.9* | 1.7* |
| 3-Amino-2-[1,1'-biphenyl]-4-yl-6-iodo-4-quinolinecarboxylic acid | 25.0 | 18 | 1.2* | 1.1* |
| 3-Amino-2-(4-phenoxyphenyl)-4-quinolinecarboxylic acid | 50.0 | 9 | 2.4* | 1.9* |
| 3-(Amino-2-[1,1'-biphenyl]-4-yl-6,8-dichloro-4-quinolinecarboxylic acid | 12.5 | 18 | 1.9* | 1.3* |
| 3-Amino-2-[1,1'-biphenyl]-4-yl-6-ethyl-4-quinolinecarboxylic acid | 25.0 | 9 | 1.3* | 1.0* |
| 3-Amino-6-fluoro-2-(2'-fluoro[1,1'-biphenyl]-4-yl)-4-quinolinecarboxylic acid | 3.13 | 18 | 1.1* | 1.2* |
| 3-Amino-2-[1,1'-biphenyl]-4-yl-6-fluoro-4-quinolinecarboxylic acid, monosodium salt | 12.5 | 18 | 1.5* | 0.8* |
| 3-(Acetylamino)-2-[1,1'-biphenyl]-4-yl-6-fluoro-4-quinolinecarboxylic acid | 25.0 | 9 | 3.8 | 3.2 |
| 3-Amino-6-chloro-2-(2'-fluoro[1,1'-biphenyl]-4-yl)-4-quinolinecarboxylic acid | 3.13 | 18 | 1.3* | 0.7* |
| 3-Amino-6-fluoro-2-[4-(trifluoromethyl)phenyl]-4-quinolinecarboxylic acid | 25.0 | 18 | 0.3* | 0.3* |
| 3-Amino-6-fluoro-2-[4-(phenylthio)phenyl]-4-quinolinecarboxylic acid | 12.5 | 9 | 2.3* | 2.1* |
| 3-Amino-6-trifluoromethyl-2-(2'-fluoro-[1,1'-biphenyl]-4-yl)-4-quinolinecarboxylic acid | 3.13 | 18 | 1.5* | 1.1* |
| 3-Amino-6-fluoro-2-(4-chlorophenyl)-4-quinolinecarboxylic acid | 25.0 | 9 | 3.9 | 3.1 |
| 3-Amino-2-(4-chlorophenyl)-4-quinolinecarboxylic acid | 25.0 | 9 | 2.7 | 2.8 |
| 3-Amino-6,8-dichloro-2-(4-chlorophenyl)-4-quinolinecarboxylic acid | 25.0 | 9 | 3.1 | 3.3 |
| 3-Amino-6-fluoro-2-(4-bromophenyl)-4-quinolinecarboxylic acid | 25.0 | 9 | 2.4 | 2.9 |
| 3-Amino-6-chloro-2-(4-bromophenyl)-4-quinolinecarboxylic acid | 25.0 | 9 | 3.1 | 2.7 |
| 3-Amino-6-chloro-2-(4-iodophenyl)-4-quinolinecarboxylic acid | 25.0 | 18 | 2.0* | 2.6 |
| 3-Amino-2-[1,1'-biphenyl]-4-yl-6-trifluoromethyl)-4-quinolinecarboxylic acid | 25.0 | 9 | 2.3* | 1.1* |
| 3-Amino-6-trifluoromethyl-2-(4-phenoxyphenyl)-4-quinolinecarboxylic acid | 25.0 | 9 | 1.4 | 2.4* |
| 3-Amino-6-trifluoromethyl-2-[4-(trifluoromethyl)phenyl]-4-quinolinecarboxylic acid | 25.0 | 18 | 0.2* | 0.3* |
| 3-Amino-2-(2'-fluoro[1,1'-biphenyl]-4-yl)-4-quinolinecarboxylic acid | 12.5 | 9 | 2.7 | 0.9* |
| 3-Amino-6-iodo-2-(2'-fluoro[1,1'-biphenyl]-4-yl)-4-quinolinecarboxylic acid | 12.5 | 9 | 1.3* | 1.3* |
| 3-Amino-6-fluoro-2-(4-iodophenyl)-4-quinolinecarboxylic acid | 25.0 | 9 | 2.9 | 2.4 |
| *3-Amino-6-fluoro-2-(2',4'-difluoro[1,1'-biphenyl]-4-yl)-4-quinolinecarboxylic acid | 3.13 | 18 | 1.9* | 2.1* |
| 3-Amino-6-chloro-2-(2',4'-difluoro[1,1'-biphenyl]-4-yl)-quinolinecarboxylic acid | 6.25 | 18 | 1.9* | 1.5* |
| 3-Amino-2-(2',4'-difluoro[1,1'-biphenyl]-4-yl-quinolinecarboxylic acid | 12.5 | 18 | 2.0* | 1.9* |
| 3-Amino-6-chloro-2-(4'-fluoro[1,1'-biphenyl]-4-yl)-4-quinolinecarboxylic acid | 6.25 | 18 | 1.1* | 1.0* |

*Statistically significant suppression of X-Ray Score relative to the arthritic controls.
p = < .05 by Student's t test The compounds of this invention may be orally administered to treat arthritis, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups and the like. Such compositions and preparations should contain at least 0.1% of active compound. The percentage of active compound in these compositions may, of course, be varied and may conveniently be between about 2% to about 60% of the weight of the unit. The amount of active compound in such therapeutically useful compositions is such that a suitable dosage will be obtained. Preferred compositions according to this invention are prepared so that an oral dosage unit contains between about 50 and 250 mg of active compound.

The tablets, capsules and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin.

When the dosage unit form is a capsule it may contain, in addition to materials of the above type, a liquid carrier such as a fatty oil.

Various other materials may be present as a coating or to otherwise modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and flavoring such as cherry or orange flavor.

These active compounds may also be administered parenterally. Solutions or suspensions of these active compounds can be prepared in water, suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be described in greater detail in conjunction with the following non-limiting examples:

EXAMPLE 1

2-Amino-4'-phenylacetophenone, hydrochloride

To 400 ml of chloroform in a 3 liter flask equipped with a mechanical stirrer was added 50 g of 2-bromo-4'-phenylacetophenone and 26.4 g of hexamethylenetetramine. The solution was stirred at 48° C. for 4 hours, then cooled to 20° C., and the resulting solid collected and washed with a small amount of absolute ethanol. The solid was suspended in a solution of 270 ml of absolute ethanol and 134 ml of concentrated hydrochloric acid and stirred at 20° C. for 22 hours. This solid was collected washed with 100 ml of water and dried at 75° C. in vacuo, giving 54.9 g of the desired compound as a white solid, mp 260° C.

EXAMPLE 2

3-Amino-2-[1,1'-biphenyl]-4-yl-6-fluoro-4-quinolinecarboxylic acid

A 21.35 g portion of 5-fluoroisatin was suspended in 175 ml of water in a three-necked 2 liter flask equipped with a reflux condenser and addition funnel. To the suspension was added a solution of 28.5 g of sodium hydroxide in 100 ml of water, then the mixture was heated to 90° C. A solution of 44.08 g of 2-amino-4'-phenylacetophenone, hydrochloride in 550 ml of a 1:1 mixture of ethanol:water was warmed slightly, then 200 ml of tetrahydrofuran was added to effect dissolution. This solution was added dropwise to the hot solution of 5-fluoroisatin over 2.75 hours with vigorous stirring. When addition was complete the solution was stirred at 90° C. for 2 hours, then the organic solvents were removed by distillation at 85° C. The remaining solution was cooled, added to 1 liter of water and the red solids collected, washed with water and saved. The filtrate was acidified to pH 5 with glacial acetic acid and the resulting yellow solid collected, washed with water and saved. The red solids saved above were stirred in a mixture of 3 liters of water and 100 ml of ammoninum hydroxide for 1 hour, then filtered and the filtrate acidified to pH 5 with glacial acetic acid. The resulting yellow solid was collected, washed with water, combined with the yellow solid saved above and dried, giving 26.9 g of the desired product, mp 229°–232° C. (dec.).

EXAMPLE 3

3-Amino-2-[1,1'-biphenyl]-4-yl-4-quinolinecarboxylic acid

A 4.42 g portion of isatin was suspended in 25 ml of water in a three-necked 1 liter flask equipped with a reflux condenser and addition funnel. To this suspension was added a solution of 6.4 g of sodium hydroxide in 20 ml of water, then the mixture was heated to 90° C. A solution of 15.0 g of 2-amino-4'-phenylacetophenone, hydrochloride in 300 ml of a 50:50 mixture of ethanol:water was warmed slightly, then 100 ml of tetrahydrofuran was added to effect dissolution. This solution added dropwise to the hot solution of isatin over 1.5 hours with vigorous stirring. When addition was complete, the solution was stirred at 90° C. for 1 hour and then the organic solvents were removed by distillation at 85° C. The remaining solution was cooled, filtered and the filtrate acidified to pH 5 with glacial acetic acid. The resulting solid was collected, washed with water and dried. The yellow solids were suspended in 40 ml of ethanol, filtered and dried, giving 2.19 g of the desired product, mp 223°–225° C. (dec.).

EXAMPLE 4

3-amino-2-[1,1'-biphenyl]-4-yl-6-bromo-4-quinolinecarboxylic acid

A 5.0 g portion of 5-bromoisatin was suspended in 25 ml of water in a three-necked 1 liter flask equipped with a reflux oondenser and addition funnel. A solution of 4.36 g of sodium hydroxide in 20 ml of water was added and the mixture heated to 90° C. A solution of 9.9 g of 2-amino-4'-phenylacetophenone hydrochloride in 200 ml of a 50:50 mixture of ethanol:water was warmed slightly, then 100 ml of tetrahydrofuran was added to effect solution. This solution was added dropwise to the hot 5-bromoisatin solution over 1.5 hours with vigorous stirring. When addition was complete, the mixture was stirred at 90° C. for 1 hour, then the organic solvents were removed by distillation at 85° C. The solution was cooled and the red solids collected, washed with water and saved. The red solid saved above was suspended in 1 liter of water, stirred for 1 hour and then filtered. The filtrate was acidified to pH 5 with glacial acetic acid and the resulting yellow solids collected and washed with water. The second crop was pure giving 3.80 g of the desired product, mp 239°–240° C. (dec.).

EXAMPLE 5

2-Amino-4'-phenoxyacetophenone hydrochloride

To a stirred solution of 29.0 g of 2-bromo-4'phenoxyacetophenone in 1800 ml of toluene was added 14.6 g of hexamethylenetetramine. The mixture was stirred at 60° C. for 4 hours and then cooled. The resulting solid was collected and washed with toluene and ether, giving 40.3 g of a white solid, mp 155°–156° C. The 40.3 g of white solid was suspended in 210 ml of ethanol and 73.5 ml of concentrated hydrochloric acid was added. This mixture was stirred at 20° C. for 18 hours, then the solid was collected and washed with ethanol and water, giving 21.2 g of the desired compound, mp 210°–215° C.

EXAMPLE 6

3-Amino-6-fluoro-2-(4-phenoxyohenyl)-4-quinolinecarboxylic acid

A 4.13 g portion of 5-fluoroisatin was suspended in 36 ml of water in a three necked 500 ml flask equipped with a reflux condenser and addition funnel. To this suspension was added a solution of 5.62 g of sodium hydroxide in 20 ml of water, followed by heating to 90° C. A solution of 9.24 g of 2-amino-4'-phenoxyacetophenone hydrochloride in 12 ml of a 50:50 mixture of ethanol:water was warmed slightly and added dropwise to the hot 5-fluoroisatin solution over 1.6 hours with vigorous stirring. When the addition was complete the solution was stirred at 90° C. for 2 hours, then the ethanol was removed by distillation at 85° C. The remaining solution was cooled to 25° C. and filtered. The filtrate was acidified to pH 5 with glacial acetic acid. The resulting solid was collected, washed with water, dried and recrystallized from 300 ml of hot acetonitrile, giving 7.3 g of the desired product, mp 228° C. (dec.).

EXAMPLE 7

5-[1,1'-Biphenyl]-4-yl-9-fluoro-3-methyl-1H-[1,3]oxazino[4,5-c]quinolin-1-one

To a suspension of 4 g of 3-amino-2-[1,1'-biphenyl]-4-yl-6-fluoro-4-quinolinecarboxylic acid in 30 ml of acetic anhydride was added 10 drops of concentrated sulfuric acid. The mixture was heated at 90° C. for 2 hours, then cooled and poured into 200 ml of water. This solution was stirred at 20° C. for 30 minutes, then the resulting solid was collected and washed with water. The residue was dissolved in 150 ml of dichloromethane and washed with 100 ml of saturated aqueous sodium bicarbonate. The organic layer was separated, dried and the volatiles removed in vacuo. The residue was dissolved in a small amount of dichloromethane and passed through a short pad of hydrous magnesium silicate, eluting with dichloromethane:hexane 1:1). The solids which were obtained were recrystallized from dichloromethane/hexane, giving 4.1 g of the desired intermediate as yellow crystals, mp 188°–189° C.

EXAMPLE 8

2-[1,1'-Biphenyl]-4-yl-3-(ethylamino)-6-fluoro-4-quinolinecarboxylic acid

To a solution of 4.0 g of 5-[1,1'-biphenyl]-4-yl-9-fluoro-3-methyl-1H-[1,3]oxazino[4,5-c] quinoline-1-one in 200 ml of tetrahydrofuran at 0° C. was added 0.91 g of sodium borohydride. The solution was stirred at 0° C. for 1 hour, then allowed to warm to 20° C. and stirred for 12 hours. A 50 ml portion of water was added and the foaming solution stirred for 10 minutes. The volatiles were removed in vacuo, then 40 ml of 0.5N sodium hydroxide was added and the solution extracted with two 100 ml portions of dichloromethane. The extracts were combined, extracted with 100 ml of water containing 5 ml of 1N sodium hydroxide and the aqueous layer from this extraction extracted with 100 ml of dichloromethane. The aqueous layers were combined, filtered through celite and acidified to pH 4 with 3% aqueous hydrochloric acid. The resulting solid was collected, washed with water and dried, giving 2.8 g of the desired product as a yellow solid, mp 180°–182° C. (dec.)

EXAMPLE 9

2-1,1'-Biphenyl]-4-yl-6-fluoro-3-(methylamino)-4-quinolinecarboxylic acid

A 10 ml portion of 95% formic acid was added dropwise to a 0° C. solution of 20 ml of acetic anhydride. This solution was heated to 60° C. for 15 minutes, then 3.9 g of 3-amino-2-[1,1'-biphenyl]-4-yl-6-fluoro-4-quinolinecarboxylic acid was added and this solution was stirred at 90° C. for 3 hours. After cooling, the solution was poured into 600 ml of water and stirred 15 minutes. The resulting solid was collected, washed with water, dried at high vacuum and 110° C. for 2 days, then dissolved in 250 ml of dry tetrahydrofuran and cooled to 0° C. A 922 mg portion of sodium borohydride was added, the reaction was stirred at 0° C. for 1 hour, then allowed to warm to 20° C. and stirred for 8 hours. A 50 ml portion of water was added and the solution stirred until foaming ceased. A 10 ml portion of 1N sodium hydroxide was added and the volatiles were removed in vacuo. The residue was partitioned between 250 ml of water and 100 ml of dichloromethane. The aqueous layer was washed with 100 ml of dichloromethane. The organic layers were combined and washed with 100 ml of water containing 5 ml of 1N sodium hydroxide. This second aqueous layer was extracted with 100 ml of dichloromethane. The combined aqueous layers were filtered through celite and then acidified to pH 4 with 5% aqueous hydrochloric acid. The resulting solid was collected, washed with water, dried and recrystallized from acetonitrile, giving 2.2 g of the desired product as yellow needles, mp 198°–200° C.

EXAMPLE 10

3-(Acetylamino)-2-[1,1'-biphenyl]-4-yl-6-fluoro-4-quinolinecarboxylic acid

A 1.8 g portion of 5-[1,1'-biphenyl]-4-yl-9-fluoro-3-methyl-1H-[1,3]oxazino[4,5-c]quinolin-1-one was dissolved in 50 ml of tetrahydrofuran. To this was added 10 ml of water containing 0.94 ml of 1N sodium hydroxide. This mixture was stirred for 4 hours, then poured into 500 ml of water and acidified to pH 4 with 3% aqueous hydrochloric acid. The resulting solid was collected, washed with water and dried at 110° C. in vacuo, giving 1.6 g of the desired product as a white solid mp 256°-259° C.

EXAMPLE 11

3-(Acetylethylamino)-2-[1,1'-biphenyl]-4-yl-6-fluoro-4-quinolinecarboxylic acid

A 2.8 g portion of 2-[1,1'-biphenyl]-4-yl-3-(ethylamino)-6-fluoro-4-quinolinecarboxylic acid was suspended in 25 ml of acetic anhydride. To this suspension was added 5 drops of concentrated sulfuric acid, then the mixture was heated at 80° C. for 2 hours. The solution was cooled, added to 200 ml of water and stirred for 30 minutes. The resulting solid was collected, washed with water, then dichloromethane and dried at 110° C. in vacuo, giving 2.0 g of the desired product as a pale yellow solid, mp 260°-262° C.

EXAMPLE 12

3-Amino-2-[1,1'-biphenyl]-4-yl-6-chloro-4-quinolinecarboxylic acid

A 3.63 g portion of 5-chloroisatin was added to 35 ml of water in a three-necked, 500 ml flask. A solution of 5.6 g of sodium hydroxide in 20 ml of water was added and the mixture was stirred at 90° C. A solution of 7.43 g of 2-amino-4'-phenylacetophenone hydrochloride in 93 ml of ethanol:water (1:1) was warmed, 25 ml of tetrahydrofuran added to maintain solution and this solution added dropwise to the 5-chloroisatin solution over 3 hours. The solvent was distilled off at 85° C. The remaining solution was cooled, 50 ml of water added and this mixture stirred for 10 minutes. The resulting red solid was collected, dried, stirred in 2.5 liters of water for 1.5 hours and filtered. The filtrate was acidified to pH 4, then the resulting solid was collected, washed with water and dried, giving 5.15 g of the desired product as a yellow solid, mp 244°-245° C.

EXAMPLE 13

3-Amino-2-[1,1'-biphenyl]-4-yl-6-iodo-4-quinolinecarboxylic acid

A 5.46 g portion of 5-iodoisatin was added to 55 ml of water in a three-necked 500 ml flask. A solution of 5.60 g of sodium hydroxide in 20 ml of water was added and the mixture was stirred at 90° C. A solution of 7.43 q of 2-amino-4'-phenylaoetophenone hydrochloride in 100 ml of ethanol:water (1:1) was warmed and 25 ml tetrahydrofuran added to maintain solution. This solution was then added dropwise to the 5-iodoisatin solution over 2.25 hours. The solvent was removed by distillation at 85°-90° C. The remaining solution was stirred overnight at room temperature, then 60 ml of water was added, followed by stirring for 20 minutes. The tan solid was collected, stirred with 2 liters of water for 2 hours, then filtered. The filtrate was acidified to pH 5 with glacial acetic acid. The resulting solid was collected, washed with water and dried, giving 6.26 g of the desired product as a yellow solid, mp 266° 267° C.

EXAMPLE 14

3-Amino-2-(4-phenoxvphenvl)-4-quinolinecarboxylic acid

A 3.68 g portion of isatin was suspended in 36 ml of water. A solution of 5.62 g of sodium hydroxide in 20 ml of water was added and the mixture was heated to 90° C. A solution of 9.24 g of 2-amino-4'-phenylacetophenone in 122 ml of ethanol:water (1:1), containing sufficient tetrahydrofuran to effect solution was added dropwise to the isatin solution over 2 hours. This mixture was stirred at reflux for 2 hours, then the solvent was distilled off. The remaining solution was cooled in an ice bath, then filtered and the filtrate acidified to pH 5. The resulting solid was collected, washed with water and air dried, then recrystallized from acetonitrile. This solid was suspended in 200 ml of water, basified with sodium hydroxide and extracted with dichloromethane. The aqueous remainder was filtered and the filtrate acidified to pH 3 with glacial acetic acid. The solid was collected and dried in vacuo, giving 3.80 g of the desired product, mp 218°-220° C.

EXAMPLE 15

3-Amino-2-[1,1'-biphenyl]-4-yl-6,8-dichloro-4-quinolinecarboxylic acid

A 3.02 g portion of 5,7-dichloroisatin was suspended in 25 ml of water in a 500 ml three-necked flask. A solution of 3.96 g of sodium hydroxide in 15 ml of water was added and the mixture heated to 90° C. A 6.0 g portion of 2-amino-4'-phenylacetophenone hydrochloride was dissolved in a mixture of 80 ml of absolute ethanol:water (1:1) and 20 ml of tetrahydrofuran. This solution was kept warm and with stirring, added dropwise to the 5,7-dichloroisatin solution over 1.5 hours. The resulting solution was refluxed 1.5 hours, then the solvent was distilled off at 85° C. The red solids were collected and washed with 50 ml of water. These solids were then stirred in 1800 ml of water, filtered and the filtrate acidified to pH 5 with glacial acetic acid. The resulting orange solids were collected and dried, giving 3.25 g of the desired product, mp 244°-245° C.

EXAMPLE 16

3-Amino-2-[1.1'-biphenyl]-4-yl-6-ethyl-4-quinolinecarboxylic acid

A 5.26 g portion of 5-ethylisatin was suspended in 43 ml of water in a 500 ml three-necked flask. A solution of 8.56 g of sodium hydroxide in 32 ml of water was added to the 5-ethylisatin solution and the mixture heated to 90° C.

A 12.63 g portion of 2-amino-4'-phenylacetophenone, hydrochloride was dissolved in a mixture of 168 ml of absolute ethanol:water (1:1) and 40 ml of tetrahydrofuran. This solution was kept warm and with stirring, added dropwise to the 5-ethylisatin solution over 2 hours. The mixture was refluxed for 2 hours, then the solvent was distilled off at 85° C. and the reaction cooled for 1 hour. The red solids were collected, stirred with 2 liters of water for 1.5 hours and then filtered. The filtrate was acidified to pH 5 with glacial acetic acid. The resulting yellow solids were collected and dried, giving 4.47 g of the desired product, mp 240°-241° C.

EXAMPLE 17

2-Amino-1-(2'-fluoro[1,1'-biphenyl-4-yl)-ethanone, hydrochloride

To a stirred solution of 34.8 g of 2-bromo-1-(2'-fluoro[1,1'-biphenyl]-4-yl)ethanone in 1600 ml of toluene was added 17.34 g of hexamethylenetetramine. The mixture was stirred at 60° C. for 4 hours and then cooled. The resulting solid was collected, washed with toluene and ether and dried, giving 48.7 g of 1-[2-(2'- fluoro[1,1'-biphenyl]-4-yl)-2-oxoethyl]-3,5,7-triaza-1-azoniatricyclo[3.3.1.1³,⁷]decane bromide as a white solid mp 174°–178° C.

To a stirred suspension of 47.7 g of the above triaza compound in 300 ml of ethanol was added 86 ml of concentrated hydrochloric acid. The mixture was stirred for 18 hours, the solid collected, washed with ethanol and water and dried, giving 26.7 g of the desired compound as white solid, mp 235°–240° C. (dec.).

EXAMPLE 18

3-Amino-6-fluoro-2-(2'-fluoro[1,1'-biphenyl]-4-yl)-4-quinolinecarboxylic acid

To a stirred suspension of 4.13 g of 5-fluoroisatin in 40 ml of water was added a solution of 5.62 g of sodium hydroxide in 20 ml of water. This mixture was heated to 85°–90° C. and a warm solution of 9.3 g of 2-amino-1-(2'-fluoro[1,1'-biphenyl]-4-yl)ethanone, hydrochloride in 140 ml of ethanol:water (1:1) and 30 ml of tetrahydrofuran was added dropwise over 2 hours. This mixture was stirred at reflux for 2 hours, then the ethanol was distilled off. The reaction was filtered and the filtrate acidified to pH 4–5 with acetic acid. The resulting solid was collected, washed with water and crystallized from 400 ml of hot ethanol, giving 7.45 g of the desired product as a yellow solid, mp 248°–250° C.

EXAMPLE 19

3-Amino-2-[1,1'-biphenyl]-4-yl-6-fluoro-4-quinolinecarboxylic acid, monosodium salt To a stirred suspension of 4.0 g of 3-amino-2-[1,1'-biphenyl]-4-yl-6-fluoro-4-quinolinecarboxylic acid in 200 ml of water was added sufficient 5N sodium hydroxide to produce solution and then an excess. The resulting solid was collected, washed with water and ether and dried, giving 1.9 g of the desired product as a tan solid, mp 325° C.

EXAMPLE 20

3-Amino-6-chloro-2-(2'-fluoro[1,1'-biphenyl]-4-yl)-4-quinolinecarboxylic acid

To a stirred suspension of 4.54 g of 5-chloroisatin in 40 ml of water was added a solution of 5.62 g of sodium hydroxide in 20 ml of water. To the resulting solution at 85°–90° C. was added dropwise over 2 hours, a warm solution of 9.3 g of 2-amino-1-(2'-fluoro[1,1'-biphenyl]-4-yl)ethanone, hydrochloride in 70 ml of water, 70 ml of ethanol and 30 ml of tetrahydrofuran. This mixture was stirred at reflux for 2 hours then the ethanol was distilled off. The reaction was cooled in an ice bath, the solid collected and washed with water. This solid was stirred in 800 ml of water for 2 hours and then filtered. The filtrate was acidified to pH 4–5 with acetic acid. The resulting solid was collected, washed with water and dried, giving 6.6 g of the desired product as a yellow solid, mp 247°–249° C.

EXAMPLE 21

2-Amino-1-[4-(phenylthio)phenyl]ethanone, hydrochloride

A 50.0 g portion of 4-acetyl diphenylsulfide was dissolved in a mixture of 118 ml of dioxane and 13 ml of ether. A 5.64 ml portion of bromine was added over 15 minutes, the mixture was stirred for 1 hour, then 2.25 ml of bromine was added. After stirring an additional hour, the reaction was poured over ice, diluted with ether and stirred. The ether layer was separated, washed with saturated sodium bicarbonate and brine, dried and filtered. The filtrate was evaporated to a dark golden oil. This oil was reacted with bromine in dioxane and ether as described above giving a dark green oil. This oil was purified by chromatography, giving 47.9 g of 2-bromo-1-[4-(phenylthio)phenyl]ethanone as a light brown solid, mp 46° C.

To a solution of 3.05 g of 2-bromo-1-[4-(phenylthio)phenyl]ethanone in 100 ml of toluene was added 1.45 g of hexamethylenetetramine. The mixture was heated at 60° C. for 1 hour with the addition of 50 ml of toluene to facilitate stirring. The mixture was cooled, the solids collected, washed with toluene and ether and dried, giving 3.845 g of 1-[2-oxo-2-[4-(phenylthio)phenyl]ethyl-3,5,7-triaza-1-azoniatricyclo[3.3.1.1³,⁷]decane bromide as a white solid with an undefined melting point.

To a suspension of 3.53 g of 1-[2-oxo-2-[4(phenylthio)phenyl]ethyl]-3,5,7-triaza-1-azoniatricyclo[3.3.1.1³,⁷]decane, bromide in 35 ml of ethanol was added 6 ml of concentrated hydrochloric acid. This mixture was stirred for 17 hours, then the solid was collected and washed with ethanol and ether. This solid was stirred with 15 ml of water at 0° C. for 50 minutes, then the solid was collected, washed with 20 ml of ice cold water and dried, giving 1.38 g of the desired compound as a white solid, mp 222°–224° C. (dec.).

EXAMPLE 22

3-Amino-6-fluoro-2-[4-(phenylthio)phenyl]-4-quinolinecarboxylic acid

To a suspension of 526 mg of 5-fluoroisatin in 4 ml of water was added 737 mg of sodium hydroxide in 6 ml of water. The resulting solution was heated to 80° C., then a solution of 1.254 g of 2-amino-1-[4-(phenylthio)phenyl]ethanone, hydrochloride in 8 ml of ethanol and 8 ml of water was added dropwise. After heating at reflux for 1 hour, the volatiles were removed in vacuo, 10 ml of water was added and the mixture filtered. A 60 ml portion of water was added to the filtrate which was then acidified to pH 4 with glacial acetic acid. After stirring for 25 minutes the solid was collected, washed with water and crystallized from 50 ml of hot acetonitrile, giving 442 mg of the desired product, mp 219°–221° C. (dec.).

EXAMPLE 23

2-[1,1'-Biphenyl]-4-yl-3-(dimethylamino)-6-fluoro-4-quinolinecarboxylic acid

A 4 g portion of 3-amino-2-[1,1'biphenyl]-4-yl-6-fluoro-4-quinolinecarboxylic acid was dissolved in 250 ml of acetonitrile. To this was added 2.7 ml of 40% aqueous formaldehyde and the mixture was heated at 80° C. until solution was complete. A 2.1 g portion of sodium cyanoborohydride was added and the solution stirred at 20° C. for 8 hours. Glacial acetic acid was added to pH 6, then 0.69 g of sodium borohydride was added and stirring continued at 20° C. for 72 hours. The reaction mixture was poured into 1 liter of water and adjusted to pH 4 with glacial acetic acid. The solid was collected, washed with water, dried and then twice suspended in 200 ml of hot ethanol and filtered. The solid was collected, giving 2.5 g of the desired product as a yellow powder, mp 235°–239° C. (gas solution).

EXAMPLE 24

2-Amino-1-[4-(trifluoromethyl)phenyl]ethanone, hydrochloride

To a stirred solution of 59.28 g of 2-bromo-4'-trifluoromethylacetophenone in 1800 ml of toluene was added 32.42 g of hexamethylenetetramine. The mixture was stirred at 60° C. for 4 hours and then cooled. The resulting solid was collected and washed with toluene and ether, giving 89.4 g of 1-[2-oxo-2-[4-(trifluoromethyl)phenyl]ethyl]-5,7-triaza-1-azoniatricyclo[3.3.1.1$^{3,7}$]decane bromide as a white solid, mp 141°-143° C.

To a stirred suspension of 89.4 g of the above triaza compound in 500 ml of ethanol was added 175.7 ml of concentrated hydrochloric acid. This mixture was stirred for 18 hours, then the solid was collected, washed with ethanol and water and dried, giving 47.1 g of the desired compound as a white solid, mp 254°-256° C.

EXAMPLE 25

3-Amino-6-fluoro-2-[4-(trifluoromethyl)phenyl]-4-quinolinecarboxylic acid

To a stirred suspension of 4.13 g of 5-fluoroisatin in 36 ml of water was added a solution of 5.62 g of sodium hydroxide in 20 ml of water. The stirred solution was heated to 80°-90° C. and a solution of 8.42 g of 2-amino-1-[4-(trifluoromethyl)phenyl]ethanone, hydrochloride in 61 ml of ethanol and 61 ml of water was added dropwise over 1.5 hours. When addition was complete, the mixture was refluxed for 20 minutes, then the ethanol was distilled off. The mixture was cooled in an ice bath, then filtered through celite. The filtrate was acidified to pH 4 with acetic acid, the solid collected, washed with water and recrystallized from acetonitrile, giving 6.04 g of the desired product as a yellow solid, mp 260°-262° C.

EXAMPLE 26

3-Amino-2-[1,1'-biphenyl]-4-yl-6-trifluoromethyl-4-quinolinecarboxylic acid

To a solution of 6.45 g of 5-trifluoromethylisatin (J. Org. Chem., 1344, 42, 1977) in 70 ml of 2.5N sodium hydroxide at 90°-95° C. was added a warm solution of 10.55 g of 2-amino-4'-phenylacetophenone, hydrochloride in 75 ml of water, 75 ml of ethanol and 50 ml of tetrahydrofuran over 30 minutes. The mixture was refluxed 1.5 hours, then the organic solvents were boiled off, the mixture diluted with 125 ml of water and filtered while still warm. The recovered solid was dissolved in 500 ml of hot water and filtered twice through celite. The second filtrate was acidified to pH 5 with glacial acetic acid, heated to near boiling, then cooled and the solid collected. This solid was recrystallized from acetonitrile/tetrahydrofuran, giving 5.74 g of the desired product as green crystals mp 255°-260° C. (dec.).

EXAMPLE 27

3-Amino-6-trifluoromethyl-2-(4-phenoxyphenyl)-4-quinolinecarboxylic acid

A solution of 6.45 g of 5-trifluoromethylisatin in water was reacted with 7.91 g of 2-amino-4'-phenoxyacetophenone hydrochloride (example 5) by the procedure described in example 6, giving 7.7 g of the desired compound as a yellow solid, mp 220°-225° C.

EXAMPLE 28

3-Amino-6-trifluoromethyl-2-]4-(trifluoromethyl)]-phenyl)]-4-quinolinecarboxylic acid A solution of 6.45 g of 5-trifluoromethylisatin in water was reacted with 7.2 g of 2-amino-1-[4-(trifluoromethyl)phenyl]ethanone hydrochloride (example 24), by the procedure described in example 25, giving 10.3 g of the desired compound as a yellow solid, mp 260°-262° C.

EXAMPLE 29

3-Amino-2-(2'-fluoro[1,1'-biphenyl]-4-yl)-4-qinolinecarboxylic acid

A solution of 3.68 g of isatin in water was reacted with 10.1 g of 2-amino-1-(2'-fluoro-[1,1'-biphenyl]-4-yl)-ethanone hydrochloride (example 17) by the procedure described in example 18, giving 3.86 g of the desired compound as a yellow solid, mp 249°-250° C.

EXAMPLE 30

3-Amino-6-iodo-2-(2'-fluoro]1,1'-biphenyl]-4-yl)-4-quinolinecarboxylic acid

A solution of 5.46 g of 5-iodoisatin in water was reacted with 7.44 g of 2-amino-1-(2'-fluoro-[1,1'-biphenyl]-4-yl)-ethanone hydrochloride (example 17)by the procedure described in example 18, giving 6.19 g of the desired compound as a yellow solid, mp 239°-241° C.

EXAMPLE 31

3--Amino-6-trifluoromethyl-2-(2'-fluoro[1,1'-biphenyl]-4-vl)-4-quinolinecarboxylic acid A solution of 6.45 g of 5-triflouromethylisatin in water was reacted with 7.97 g of 2-amino-1-(2'-fluoro[1,1'-biphenyl]-4-yl)-ethanone hydrochloride (example 17) by the procedure described in example 18, giving 9.0 g of the desired compound as a yellow solid, mp 255°-260° C.

EXAMPLE 32

2-Amino-1-(4-chlorophenyl)ethanone hydrochloride

To a stirred solution of 50 g of 2-bromo-4'-chloroacetophenone in 1600 ml of toluene was added 30 g of hexamethylenetetramine. The mixture was stirred for 4 hours at 60° C. and then cooled to 20° C.. The resulting solid was filtered, washed with toluene and ether, giving 79 g of a white solid, mp 141°-143° C.. To a stirred suspension of the above white soid in 400 ml of ethanol was added 150 ml of concentrated hydrochloric acid. The mixture was stirred for 18 hours. The solid was collected by filtration and washed with ethanol and water and dried, giving 46.5 g of the desired compound as a white solid, mp 265°-270° C.

EXAMPLE 33

3-Amino-6-fluoro-2-(4-chlorophenyl)-4-quinolinecarboxylic acid

To a stirred suspension of 7 g of 5-fluoroisatin in 58 ml of water was added a solution of 9.36 g of sodium hydroxide in 33 ml of water. The solution was heated to 85° C. and a solution of 12 g of 2-amino-1-(4-chlorophenyl)ethanone hydrochloride in a mixture of 92 ml of ethanol and 40 ml of tetrahydrofuran and 92 ml of water was added drop-wise over 2 hours. After the addition was complete, the solution was refluxed for an additional 30 minutes and then the ethanol and tetrahydrofuran were removed by distillation. The mixture was cooled to 20° C. and filtered through celite. The filtrate was acidified to pH 4 with acetic acid. The solid was filtered off, washed with water and dried, giving 12.8 g of the desired compound as a yellow solid, mp 241°-243° C.

EXAMPLE 34

3-Amino-2-(4-chlorophenyl)-4-quinolinecarboxylic acid

A solution of 5.8 g of isatin in water was reacted with 12.0 g of 2-amino-1-(4-chlorophenyl)ethanone hydrochloride by the procedure described in example 33, giving 8.1 g of the desired compound as a yellow solid, mp 243°-244° C.

EXAMPLE 35

3-Amino-6,8-dichloro-2-(4-chlorophenyl)-4-quinolinecarboxylic acid

A solution of 5.4 g of 5,7-dichloroisatin in water was reacted with 7.21 g of 2-amino-1-(4-chlorophenyl)ethanone hydrochloride by the procedure described in example 33, giving 5.2 g of the desired compound as a yellow solid, mp 260°-261° C.

EXAMPLE 36

3-Amino-6-chloro-2-(4-chlorophenyl)-4-quinolinecarboxylic acid

A solution of 4.54 g of 5-chloroisatin in water was reacted with 6.8 g of 2-amino-1-(4-chlorophenyl)ethanone hydrochloride by the procedure described in example 33, giving 6.27 g of the desired compound as a yellow solid, mp 240°-241° C.

EXAMPLE 37

Amino-1-(4-bromophenyl)ethanone hydrochloride

To a stirred solution of 40.0 g of 2-bromo-4'-bromoacetophenone in 1100 ml of toluene was added 20.65 g of hexamethylenetetramine. The mixture was stirred for 4 hours at 60° C. and then cooled to 20° C. The resulting solid was filtered, washed with toluene and ether, giving 59.2 g of white solid, mp 149°-150° C. To a stirred suspension of the above white solid in 225 ml of ethanol was added 105 ml of concentrated hydrochloric acid. The mixture was stirred for 18 hours. The solid was collected by filtration and washed with ethanol and water and dried, giving 39.5 g of the desired compound as a white solid, mp 275° C. (dec)

EXAMPLE 38

3-Amino-6-fluoro-2-(4-bromophenyl)-4-quinolinecarboxylic acid

To a stirred suspension of 4.13 g of 5-fluoroisatin in 40 ml of water was added a solution of 5.62 g of sodium hydroxide in 20 ml of water. The solution was heated to 85° C. and a solution 8.8 g of 2-amino-1-(4-bromophenyl)ethanone hydrochloride in a mixture of 61 ml of ethanol and 15 ml of tetrahydrofuran and 61 ml of water was added dropwise over 2 hours. After the addition was complete, the solution was refluxed for an additional 30 minutes and then the ethanol and tetrahydrofuran were removed by distillation. The mixture was cooled to 20° C. and filtered through celite. The filtrate was acidified to pH 4 with acetic acid. The solid was filtered off, washed with water and dried, giving 7.8 g of the desired compound as a yellow solid, mp 231°-233° C.

EXAMPLE 39

3-Amino-6-chloro-2-(4-bromophenyl)-4-quinolinecarboxylic acid

A solution of 5.45 g of 5-chloroisatin in water was reacted with 10.0 g of 2-amino-1-(4-bromophenyl)ethanone hydrochloride by the procedure described in example 1, giving 9.31 g of the desired compound as a yellow solid, mp 241°-242° C.

EXAMPLE 40

2-Amino-1-(4-iodophenyl)ethanone hydrochloride

To a stirred solution of 23.6 g of 2-bromo-4'-iodoacetophenone in 1000 ml of toluene was added 9.3 g of hexamethylenetetramine. The mixture was stirred for 4 hours at 60° C. and then cooled to 20° C.. The resulting solid was filtered, washed with toluene and ether, giving 30.3 g of a white solid, mp 166° C. To a stirred suspension of the above white solid in 200 ml of ethanol was added 55 ml of concentrated hydrochloric acid. The mixture was stirred for 18 hours. The solid was collected by filtration and washed with ethanol and water and dried, giving 22.4 g of the desired compound as a white solid, mp 262°-265° C.(dec).

EXAMPLE 41

3-Amino-6-chloro-2-(4-iodophenyl)-4-quinolinecarboxylic acid

To a stirred suspension of 4.17 g of 5-chloroisatin in 40 ml of water was added a solution of 5.15 g of sodium hydroxide in 18 ml of water. The solution was heated to 85° C. and a solution of 9.8 g of 2-amino-1-(4-iodophenyl)ethanone hydrochloride in a mixture of 70 ml of ethanol and 30 ml of tetrahydrofuran and 130 ml of water was added dropwise over 2 hours. After the addition was complete, the solution was refluxed for an additional 30 minutes and then the ethanol and tetrahydrofuran were removed by distillation. The mixture was cooled to 20° C. and filtered through celite. The filtrate was acidified to pH 4 with acetic acid. The solid was filtered off, washed with water and dried, giving 6.5 g of the desired compound as a yellow solid, mp 243°-245° C.

EXAMPLE 42

3-Amino-6-fluoro-2-(4-iodophenyl)-4-quinolinecarboxylic acid

A basic aqueous solution of 3.8 g of 5-fluoroisatin in water was reacted with 9.8 g of 2-amino-1-(4-iodophenyl)ethanone hydrochloride by the procedure described in example 41, giving 7.0 g of the desiredcompound as a yellow solid, mp 251°-253° C.

EXAMPLE 43

2-Amino-1-(2',4'-difluoro[1,1'-biphenyl]-4-yl)-ethanone hydrochloride

To a stirred solution of 38.8 g of 2-bromo-1(2',4'-difluoro[1,1'-biphenyl]-4-yl)-ethanone in 1100 ml of toluene was added 16.12 g of hexamethylenetetramine. The mixture was stirred for 4 hours at 60° C. hen cooled to 20°-C. The resulting solid was filtered, washed with toluene and ether, giving 52.4 g of a white solid, mp 155°-156° C. To a stirred suspension of the above white solid in 350 ml of ethanol was added 95 ml of concentrated hydrochloric acid. The mixture was stirred for 18 hours. The solid was collected by filtration and washed with ethanol and water and dried, giving 28.4 g of the title compound as a white solid, mp 242°-244° C.(dec)

EXAMPLE 44

3-Amino-6-fluoro-2-(2,4'-difluoro[1,1'-biphenyl]-4-yl)-4-quinolinecarboxylic acid A basic aqueous solution of 3.8 g of 5-fluoroisatin in water was reacted with 9.3 g of 2-amino-1-(2',4'-difluoro[1,1'-biphenyl]-4-yl)ethanone hydrochloride by the procedure described in example 20, giving 7.7 g of the desired compound as a yellow solid, mp 245°-247° C.

EXAMPLE 45

3-Amino-6-chloro-2-(2',4'-difluoro[1,1'-biphenyl]-4-yl)-4-quinolinecarboxylic acid A basic aqueous solution of 4.3 g of 5-chloroisatin in water was reacted with 9.4 g of 2-amino-1-(2',4'-difluoro[1,1'-biphenyl]-4-yl)ethanone hydrochloride by the procedure described in example 20, giving 6.1 g of the desired compound as a yellow solid, mp 253°-254° C.

EXAMPLE 46

3-Amino-2-(2',4'-difluoro[1,1'-biphenyl]-4-yl)-4-quinolinecarboxylic acid

A basic aqueous solution of 3.5 g of isatin in water was reacted with 9.3 g of 2-amino-1-(2',4'-difluoro[1,1'-biphenyl]-4-yl)ethanone hydrochloride by the procedure described in example 20, giving 2.8 g of the desired compound as a yellow solid, mp 244°-247° C.

EXAMPLE 47

2-Amino-1-(4'-fluoro1,1'-biphenyl]-4-yl)ethanone hydrochloride

To a stirred solution of 22.3 g of 2-bromo-1-(4'-fluoro[1,1'-biphenyl]-4-yl)ethanone in 1000 ml of toluene was added 11.2 g of hexamethylenetetramine. The mixture was stirred for 4 hours at 60° C. and then cooled to 20° C. The resulting solid was filtered, washed with toluene and ether, giving 30.4 g of a white solid, mp 155°-156° C. To a stirred suspension of the above white solid in 190 ml of ethanol was added 55 ml of concentrated hydrochloric acid. The mixture was stirred for 18 hours. The solid was collected by filtration and washed with ethanol and water and dried, giving 18.4 g of the desired compound as a white solid, mp 335°-345° C.(dec).

EXAMPLE 48

3-Amino-6-chloro-2-(4'-fluoro[1,1'-biphenyl]-4-yl)-4-quinolinecarboxylic acid

A basic aqueous solution of 4.54 g of 5-chloroisatin in water was reacted with 9.0 g of 2-amino-1-(4'-fluoro[1,1'-biphenyl]-4-yl)ethanone hydrochloride by the procedure described in example 20, giving 6.2 g of the desired compound as a yellow solid, mp 255°-257° C.

EXAMPLE 49

3-Amino-6-fluoro-2-(4'-fluoro[1,1'-biphenyl]-4-yl)-4-quinolinecarboxylic acid

A basic aqueous solution of 4.13 g of 5-fluoroisatin in water was reacted with 9.3 g of 2-amino-1-(4'-fluoro-[1,1'-biphenyl]-4-yl)-ethanone hydrochloride by the procedure described in example 20, giving 7.13 g of the desired compound as a yellow solid, mp 241°-243° C.

EXAMPLE 50

3-Amino-6-fluoro-2-(4-iodophenyl)-4-quinolinecarboxylic acid methyl ester

To a solution of 400 ml of acetonitrile and 40 ml of tetrahydrofuran was added 4.0 g of 3-amino-6-fluoro-2-(4-iodophenyl)-4-quinolinecarboxylic acid and 2.0 g of cesium carbonate. The solution was stirred for 1 hour and 0.84 ml of methyl iodide was added. After stirring for an additional 12 hours, the volatiles were removed in vacuo and the residue dissolved in methylene chloride and ethyl acetate. The insoluble solids were removed by filtration and the volatiles removed from the filtrate in vacuo. The yellow solid obtained was recrystallized from methylene chloride, giving 3.45 g of the desired compound as yellow crystals, mp 223°-225° C.

EXAMPLE 51

3-Amino-6-fluoro-2-[4-(3-pyridinyl)-phenyl]-4-quinolinecarboxylic acid methyl ester To a degassed solution of 0.39 g of 3-amino-6-fluoro-2-(4-iodophenyl)-4-quinolinecarboxylic acid methyl ester and 0.035 g of tetrakis(triphenylphosphine) palladium in 10 ml of tetrahydrofuran and 10 ml toluene was added 1.0 ml of 2M aqueous sodium carbonate followed by a solution of 0.148 g of 3-pyridine boronic acid in 2 ml of ethanol. The mixture was stirred at reflux under argon for 5 hours and then cooled to 20° C. Two drops of 30% hydrogen peroxide were added and the mixture stirred for 30 minutes. The reaction mixture was partitioned between water and methylene chloride The organic layers were washed with water and dried over sodium sulfate. The volatiles were removed in vacuo, giving a tan powder. The crude product was purified via silica gel chromatography using toluene/acetone/-methanol 78:20:2 as the eluent. The desired compound was obtained as yellow crystals (0.132g), mp 178°-183° C.

EXAMPLE 52

3-Amino-6-fluoro-2-[4-(3-pyridinyl)phenyl]-4-quinolinecarboxylic acid

To a solution of 0.097 g of 3-amino-6-fluoro-2-[4-(3-pyridinyl)-phenyl]-4-quinolinecarboxylic acid methyl ester in 10 ml of ethanol was added 1.0 ml of 2.5N aqueous sodium hydroxide. The solution was stirred at reflux for 0.5 hour. The solution was concentrated to a small volume in vacuo and then diluted with 10 ml of water. The solution was acidified with 0.2 ml of glacial acetic acid, warmed briefly and cooled to 20° C. The solid was collected, washed with water, and dried in vacuo, giving 0.076 g of the desired compound as a yellow powder, mp 260°-268° C.

We claim:

1. A compound of the formula:

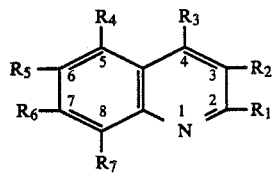

wherein $R_1$ is selected from the group consisting of

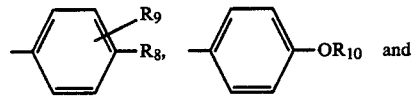

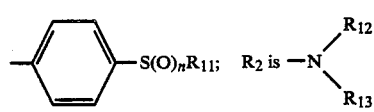

$R_3$ is selected from the group consisting of

(where A is an alkali or alkaline earth metal); $R_4$, $R_5$, $R_6$ and $R_7$ are independently selected from the group consisting of hydrogen, halogen, alkyl ($C_1$–$C_6$), trifluoromethyl and —O—alkyl($C_1$–$C_3$), with the proviso that least two of $R_4$, $R_5$, $R_6$ and $R_7$ must be hydrogen; $R_8$ is selected from the group consisting of straight or branched chain alkyl($C_1$–$C_{12}$), halogen, cycloalkyl(-$C_3$–$C_7$) trifluoro methyl, hydroxy, phenyl and 2-fluorophenyl and pyridyl; $R_{10}$ is selected from the group consisting of

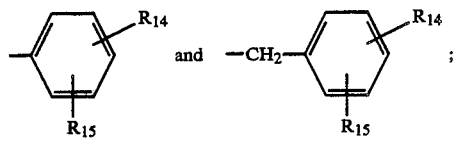

$R_2$ is selected from the group consisting of hydrogen and alkyl($C_1$–$C_6$); $R_{13}$ is selected from the group consisting of

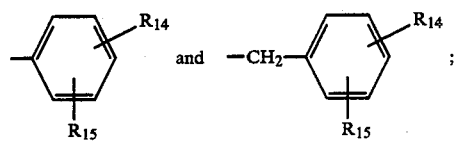

hydrogen, alkyl ($C_1$–$C_6$),

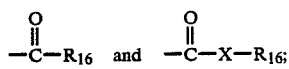

$R_{16}$ is alkyl($C_1$–$C_6$),

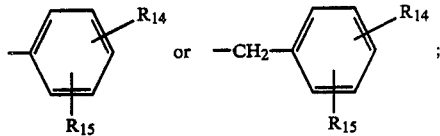

X is —O—, —S—, —NH— or $NR_{16}$; $R_{11}$ is selected from the group consisting of straight or branched chain alkyl($C_1$–$C_{12}$), cycloalkyl($C_1$–$C_7$), trifluoromethyl, hydroxy, phenyl and 2-fluorophenyl; $R_9$, $R_{14}$, and $R_{15}$ are independently selected from the group consisting of hydrogen, halogen, nitro, alkyl($C_1$–$C_5$), alkoxy($C_1$–$C_5$), alkylthio($C_1$–$C_5$), hydroxy, trifluoromethyl and amino; n is an integer from zero to two inclusive; and the pharmacologically acceptable salts thereof.

2. The compound according to claim 1, 3-amino-2-[1,1'-biphenyl]-4-yl-6-fluoro-4-quinolinecarboxylic acid.

3. The compound according to claim 1, 3-amino-2-[1,1'-biphenyl]-4-yl-4-quinolinecarboxylic acid.

4. The compound according to claim 1, 3-amino-2-[1,1'-biphenyl]-4-yl-6-bromo-4-quinolinecarboxylic acid.

5. The compound according to claim 1, 3-amino-6-fluoro-2-(4-phenoxyphenyl)-4-quinolinecarboxylic acid.

6. The compound according to claim 1, 2-[1,1'-biphenyl]-4-yl-3-(ethylamino)-6-fluoro-4-quinolinecarboxylic acid.

7. The compound according to claim 1, 2-[1,1'-biphenyl]-4-yl-6-fluoro-3-(methylamino)-4-quinolinecarboxylic acid.

8. The compound according to claim 1, 3-(acetylamino)-2-[1,1'-biphenyl]-4-yl-6-fluoro-4quinolinecarboxylic acid.

9. The compound according to claim 1, 3-(acetylethylamino)-2-[1,1'-biphenyl]-4-yl-6-fluoro-quinolinecarboxylic acid.

10. The compound according to claim 1, 3-amino-2-[1,1'-biphenyl]-4-yl-6-chloro-4-quinolinecarboxylic acid.

11. The compound according to claim 1, 3-amino-2-[1,1'-biphenyl]-4-yl-6-iodo-4-quinolinecarboxylic acid.

12. The compound according to claim 1, 3-amino-2-(4-phenoxyphenyl)-4-quinolinecarboxylic acid.

13. The compound according to claim 1, 3-amino-2-[1,1'-biphenyl]-4-yl-6,8-dichloro-4-quinolinecarboxylic acid.

14. The compound according to claim 1, 3-amino-2-[1,1'-biphenyl]-4-yl-6-ethyl-4-quinolinecarboxylic acid.

15. The compound according to claim 1, 3-amino-6-fluoro-2-(2'-fluoro[1,1'-biphenyl]-4-yl)-4-quinolinecarboxylic acid.

16. The compound according to claim 1, 3-amino-2-[1,1'-biphenyl]-4-yl-6-fluoro-4-quinolinecarboxylic acid, monosodium salt.

17. The compound according to claim 1, 3-amino-6-chloro-2-(2'-fluoro[1,1'-biphenyl]-4-yl)-4-quinolinecarboxylic acid.

18. The compound according to claim 1, 3-amino-6-fluoro-2-[4-(phenylthio)phenyl]-4-quinolinecarboxylic acid.

19. The compound according to claim 1, 2-[1,1'-biphenyl]-4-yl-3-(dimethylamino)-6-fluoro-4-quinolinecarboxylic acid.

20. The compound according to claim 1, 3-amino-6-fluoro-2-[4-(trifluoromethyl)phenyl]-4-quinolinecarboxylic acid.

21. The compound according to claim 1, 3-amino-2-[1,1'-biphenyl]-4-yl-6-trifluoromethyl-4-quinolinecarboxylic acid.

22. The compound according to claim 1, 3-amino-6-trifluoromethyl-2-(4-phenoxyphenyl)-4-quinolinecarboxylic acid.

23. The compound according to claim 1, 3-amino-6-trifluoromethyl-2-[4-(trifluoromethyl)phenyl]-4-quinolinecarboxylic acid.

24. The compound according to claim 1, 3-amino-2-(2'-fluoro[1,1'-biphenyl]-4-yl)-4-quinolinecarboxylic acid.

25. The compound according to claim 1, 3-amino-6-iodo-2-(2'fluoro[1,1'-biphenyl]-4-yl]-4quinolinecarboxylic acid.

26. The compound according to claim 1, 3-amino-6-trifluoremethyl-2-(2'-fluoro[1,1'-biphenyl]-4-yl)-4-quinolinecarboxylic acid.

27. The compound according to claim 1, 3-amino-6-fluoro-2-(4-chlorophenyl)-4-quinolinecarboxylic acid.

28. The compound according to claim 1, 3-amino-2-(4-chlorophenyl)-4-quinolinecarboxylic acid.

29. The compound according to claim 1, 3-amino-6,8-dichloro-2-(4-chlorophenyl)-4-quinolinecarboxylic acid.

30. The compound according to claim 1, 3-amino-6-chloro-2-(4-chlorophenyl)-4-quinolinecarboxylic acid.

31. The compound according to claim 1, 3-amino-6-fluoro-2-(4-bromophenyl)-4-quinolinecarboxylic acid.

32. The compound according to claim 1, 3-amino-6-chloro-2-(4-bromophenyl-4-quinolinecarboxylic acid.

33. The compound according to claim 1, 3-amino-6-chloro-2-(4-iodophenyl)-4-quinolinecarboxylic acid.

34. The compound according to claim 1, 3-amino-6-fluoro-2-(4-iodophenyl)-4-quinolinecarboxylic acid.

35. The compound according to claim 1, 3-amino-6-fluoro-2-(2',4'-difluoro[1,1'-biphenyl]-4-yl)-4-quinolineacarboxylic acid.

36. The compound according to claim 1, 3-amino-6-chloro-2-(2',4'-difluoro[1,1'-biphenyl]-4-yl)-4-quinolinecarboxylic acid.

37. The compound according to claim 1, 3-amino-2-(2,4-difluoro[1,1'-biphenyl]-4-yl-4-quinolinecarboxylic acid.

38. The compound according to claim 1, 3-amino-6-chloro-2-(4'-fluoro[1,1'-biphenyl]-4-yl)-4-quinolinecarboxylic acid.

39. The compound according to claim 1, 3-amino-6-fluoro-2-(4'-fluoro[1,1'-biphenyl]-4-yl)-4quinolinecarboxylic acid.

40. The compound according to claim 1, 3-amino-6-fluoro-2-[4-(3-pyridinyl)-phenyl]-4-quinolinecarboxylic acid.

41. A method of inducing immunosuppression in a mammal which comprises administering to said mammal an effective amount of a compound selected from those of claim 1.

42. A method of inhibiting the progression of arthritis in a mammal which comprises administering to said mammal an effective amount of a compound selected from those of claim 1.

43. A method of inhibiting progressive joint deterioration in a mammal caused by arthritis which comprises administering to said mammal an effective amount of a compound selected from those of claim 1.

44. A composition of matter in dosage unit form, comprising an effective amount of a compound selected from those of claim 1 in association with a pharmaceutically acceptable carrier, said composition being used to inhibit the progression of arthritis or to inhibit progressive joint deterioration caused by arthritis in a mammal.

45. The composition of matter of claim 44 wherein the effective amount of the compound is from about 50 to about 250 mg of compound.

* * * * *